(12) United States Patent
Ziaee (10) Patent No.: US 6,581,601 B2
(45) Date of Patent: Jun. 24, 2003

(54) NASAL MASK WITH BALLOON EXHALATION VALVE

(76) Inventor: Saeed Ziaee, 42 Castleridge Drive, Richmond Hill (CA), L4B 1P8

( * ) Notice: Subject to any disclaimer, the term of this patent is extended or adjusted under 35 U.S.C. 154(b) by 0 days.

(21) Appl. No.: 10/041,788

(22) Filed: Oct. 19, 2001

(65) Prior Publication Data

US 2002/0096178 A1 Jul. 25, 2002

Related U.S. Application Data

(63) Continuation-in-part of application No. 09/593,813, filed on Jun. 15, 2000.
(60) Provisional application No. 60/139,721, filed on Jun. 18, 1999.

(51) Int. Cl.$^7$ .............................................. A62B 18/02
(52) U.S. Cl. .............................. 128/206.21; 128/207.12
(58) Field of Search .................... 128/200.24, 201.23, 128/201.24, 201.28, 203.29, 204.12, 205.24, 206.12, 206.15, 206.16, 206.18, 206.19, 206.21, 206.24, 206.26–206.28, 207.12, 207.13; 137/908

(56) References Cited

U.S. PATENT DOCUMENTS

| | | | | |
|---|---|---|---|---|
| 2,663,297 A | | 12/1953 | Turnberg ..................... 128/206 |
| 3,985,131 A | * | 10/1976 | Buck et al. ............. 128/204.23 |
| 4,190,045 A | * | 2/1980 | Bartels .................. 128/205.24 |
| 4,248,218 A | | 2/1981 | Fischer ................... 128/204.18 |
| 4,502,481 A | * | 3/1985 | Christian ............... 128/205.24 |
| 4,527,557 A | * | 7/1985 | DeVries et al. ........ 128/204.23 |
| 4,782,832 A | | 11/1988 | Trimble et al. ........ 128/207.18 |
| 4,821,713 A | * | 4/1989 | Bauman ................. 128/205.13 |
| 4,944,310 A | | 7/1990 | Sullivan ..................... 128/848 |
| 4,996,983 A | | 3/1991 | AmRhein ............. 128/206.11 |
| 5,042,478 A | | 8/1991 | Kopala et al. ......... 128/207.18 |
| 5,113,857 A | | 5/1992 | Dickerman et al. .... 128/207.18 |
| 5,127,400 A | * | 7/1992 | DeVries et al. ........ 128/204.23 |
| D333,015 S | | 2/1993 | Farmer et al. ................. D29/8 |
| 5,477,852 A | | 12/1995 | Landis et al. .......... 128/207.18 |
| 5,538,000 A | | 7/1996 | Rudolph ................. 128/205.25 |
| 5,542,416 A | * | 8/1996 | Chalvignac ............. 128/204.23 |
| 5,687,715 A | | 11/1997 | Landis et al. .......... 128/207.18 |
| 5,692,497 A | * | 12/1997 | Schnitzer et al. ...... 128/204.18 |
| 5,720,709 A | * | 2/1998 | Schnall ................... 128/204.21 |
| 5,724,965 A | | 3/1998 | Handke et al. ........ 128/207.13 |
| 5,813,399 A | * | 9/1998 | Isaza et al. ............. 128/204.21 |
| D402,755 S | | 12/1998 | Kwok ..................... D24/110.4 |
| 5,918,597 A | * | 7/1999 | Jones et al. ............. 128/204.23 |
| 6,019,101 A | | 2/2000 | Cotner et al. .......... 128/207.13 |
| D423,096 S | | 4/2000 | Kwok ..................... D24/110.1 |
| 6,076,523 A | * | 6/2000 | Jones et al. ............. 128/204.21 |
| 6,102,038 A | * | 8/2000 | DeVries ................. 128/204.23 |
| 6,112,746 A | | 9/2000 | Kwok et al. ........... 128/207.13 |
| 6,123,071 A | | 9/2000 | Berthon-Jones et al. . 128/204.18 |
| 6,135,108 A | * | 10/2000 | Hoenig ................... 128/204.18 |
| 6,135,109 A | | 10/2000 | Blasdell et al. ......... 128/206.28 |
| 6,173,711 B1 | * | 1/2001 | Ruton .................... 128/204.25 |
| 6,192,886 B1 | * | 2/2001 | Rudolph ................. 128/205.25 |
| 6,263,874 B1 | | 7/2001 | LeDez et al. .......... 128/206.21 |
| 6,306,099 B1 | * | 10/2001 | Morris ........................ 600/529 |
| 6,371,112 B1 | * | 4/2002 | Bibi ....................... 128/200.24 |
| 6,371,113 B1 | * | 4/2002 | Tobia et al. ............ 128/204.21 |
| 6,412,483 B1 | * | 7/2002 | Jones et al. ............. 128/204.21 |
| 6,418,928 B1 | * | 7/2002 | Bordewick et al. .... 128/205.25 |

* cited by examiner

Primary Examiner—Weilun Lo
Assistant Examiner—Teena Mitchell
(74) Attorney, Agent, or Firm—Grossman & Flight, LLC (57) ABSTRACT

A nasal mask has a shell portion that is a hollow enclosure with a rearwardly facing opening that is defined by edge portions of the shell portion. A resiliently deformable endless interface member engages and extends around the edge portion of the opening and forms a seal between the shell portion and the user's face. The shell portion and the interface member are generally symmetrical about a median place. The shell portion has two gas inlet orifices, one on each side of the median place. The shell portion has a tubular exhalation outlet extending from the face of the mask. The mask is further provided with a balloon exhalation valve connected to the exhalation outlet for alternately venting and sealing the interior of the mask during exhalation and inhalation, respectively.

19 Claims, 8 Drawing Sheets

NASAL MASK WITH BALLOON EXHALATION VALVE

CROSS-REFERENCE TO RELATED APPLICATIONS

This application is a continuation-in-part of co-pending non-provisional application 09/593,813 filed Jun. 15, 2000. Application Ser. No. 09/593,813 claims the benefit of the filing date of provisional application No. 60/139,721 filed Jun. 18, 1999.

BACKGROUND OF THE INVENTION

The present invention relates to a nasal mask. Known nasal masks of which the applicant is aware have suffered from various disadvantages. For example, known nasal masks do not prevent leakage of gas such as air or oxygen from the mask efficiently, and do not distribute forces evenly on the face of the user. With known masks, an undesirably high tensile force has to be exerted by the straps or other mask retaining devices that hold the mask to the user's head, and as a result excessive pressure tends to be exerted on the user's face, causing breakdown of the skin, for example, on the bridge of the nose. Further, known masks interfere with use of eye glasses while wearing the mask, and may present the difficulty that a gas tube may become pinched or obstructed when the user lies on one side, for example when the user is sleeping.

Another disadvantage of known masks is the build-up of exhaled $CO_2$ within the mask and the patient's mouth and airway due to an inadequate ventilation of exhaled air. This build-up is sometime referred to as "dead space". With known masks, it has been necessary to make a design trade off between providing a sealed environment for inhalation and providing a resistance-free path for exhalation with minimal dead space.

It would be advantageous to provide a nasal mask that provides both a sealed environment for inhalation and reduced resistance to exhalation with minimized dead space.

BRIEF SUMMARY OF THE INVENTION

The present invention provides a shell portion and an interface member for a nasal mask comprising a shell portion defining a hollow enclosure with a rearwardly facing opening defined by edge portions of the shell portion, and a resiliently deformable endless interface member engaging with and extending around said edge portion of the opening and adapted to form a seal between the shell portion and the user's face, and wherein the shell portion and the interface member are at least generally symmetrical about a median plane, and said shell portion has two gas inlet orifices disposed one on each side of the median plane. With this arrangement, the mask may be supplied with gas through two relatively small diameter flexible tubes coupled to the orifices, respectively. The small diameter tubes exert only relatively small tensile forces away from the user's face, and therefore only relatively small forces need to be exerted by retaining straps to retain the mask, and as a result, excessive application of force to the user's face and problems such as breakdown of skin on the bridge of the nose can be avoided. Further, the smaller tubes can be easily oriented in any desired position relative to the mask. For example, they may be positioned downwardly below the mask to facilitate wearing of eye glasses, or may be positioned centrally of the top of the user's head so that they are not obstructed if the user lies on one side.

In a preferred form, the gas inlet orifices are positioned symmetrically with respect to the median plane, and the inner side of the shell adjacent each orifice is provided with an inwardly extending tubular portion for engaging deformable nasal pillows that may form a seal between each orifice and a nostril of the user.

In one aspect, the present invention provides a nasal mask for use by a patient, the nasal mask including a shell portion, the shell portion being in sealed communication with the patient's face and having one or more inlet orifices for receiving supplied gas, the shell portion having an exhalation orifice and, adjacent the exhalation orifice, an outwardly extending tubular formation defining a flow passage through the exhalation orifice; and a balloon exhalation valve removably connected to the outwardly extending tubular formation, the balloon exhalation valve having a balloon adapted to controllably seal and unseal the flow passage.

In another aspect, the present invention provides, in combination, a nasal mask and a balloon exhalation valve, the nasal mask including a shell portion, the shell portion defining a hollow enclosure with a rearwardly facing opening defined by edge portions of the shell portion, and wherein the shell portion is at least generally symmetrical about a median plane, the shell portion having two gas inlet orifices disposed one on each side of the median plane, the front of the shell portion having an exhalation orifice approximately centred on the median plane and, adjacent the exhalation orifice, an outwardly extending tubular elbow formation defining a flow passage through the exhalation orifice, the balloon exhalation valve including a hollow tubular casing having a lower end face with a central passage therethrough, an inlet tube securely attached to the lower end face of the casing and passing through the central passage, and a balloon disposed within the casing, the mouth of the balloon being in sealed communication with the inlet tube, wherein the upper end of the casing is removably connected to the outwardly extending tubular elbow formation, and wherein the casing has an outlet orifice disposed proximate the outwardly extending tubular elbow, the outlet orifice defining a flow passage from said exhalation orifice through the casing, and wherein the balloon seals the exhalation orifice when the balloon is inflated.

Preferred embodiments of the present invention will now be described in more detail, by way of example only, with reference to the accompanying drawings.

BRIEF DESCRIPTION OF THE SEVERAL VIEWS OF THE DRAWINGS

Reference will now be made, by way of example, to the accompanying drawings which show a preferred embodiment of the present invention, and in which.

DETAILED DESCRIPTION OF THE INVENTION

Referring to the drawings wherein like reference numerals indicate like parts, a mask 20 comprises a shell portion 21 and an interface portion 22, preferably used in combination with pillow engaging members 23 and nasal pillows 24.

Figure 4:
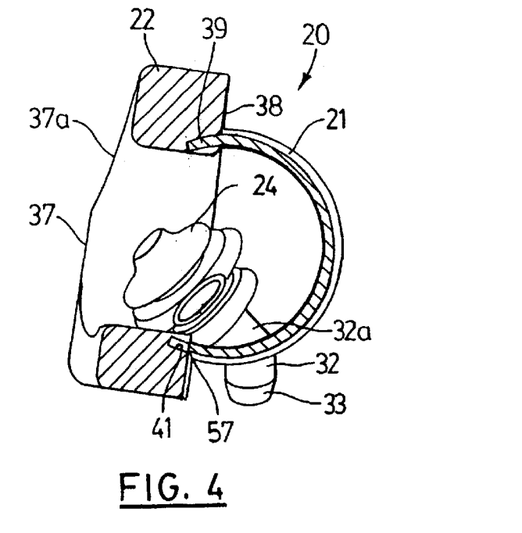
FIG. 4 shows a cross-sectional view taken on the line 4—4 in FIG. 3.

As best seen in FIGS. 1, 2, 4 and 5 shell portion 21 defines a hollow enclosure with a rearwardly facing generally triangular opening 26 defined by edges of the shell comprising a transverse top portion 27, arcuately transversely outwardly and downwardly extending side portions 28 and arcuate lower edge portions 29. The shell 21 is generally symmetrical about a median plane 3 seen in FIG. 2, and the shell portion 21 has two gas inlet orifices comprising openings 31 in the lower front portion of the shell 21. Adjacent each opening 31, the shell 21 is formed integrally with outwardly extending tubular portions 32 having slightly tapering end portions 33 defining a flow passage extending from the outer end of the tubular portions to the interior of the shell 21 through the openings 31. In the preferred form, inwardly of the shell 21 and integrally formed therewith are inwardly extending tubular portions 32a that, as seen in FIG. 4, each have their axes inclined somewhat downwardly rearwardly with respect to the axis of the outer portion 32.

In the preferred form, shell 21 comprises two part spherical portions 34 that are connected together along a bridging portion 36 coincident with the median plane. The spherical portions 34 provide especially good symmetry and distribute pressure evenly on the wearer's face and provide reentrant portions providing rearwardly directed forces urging the mask toward the wearer's face.

Each portion 34 has on each transversely outer side, at a portion intermediate the front and rear sides of the shell 21, an integrally formed strap lug 35 to which a retaining strap may be attached.

The shell portion 21 may, for example, be molded of a stiffly resilient plastics material.

The interface member 22 is preferably formed of a soft, compliant and resiliently deformable material, for example a soft silicone rubber composition that provide a cushion between the rigid shell 21 and the patient's face and conforms to and seals to the patient's face on the one hand and to the shell 21 on the other.

Figure 1:
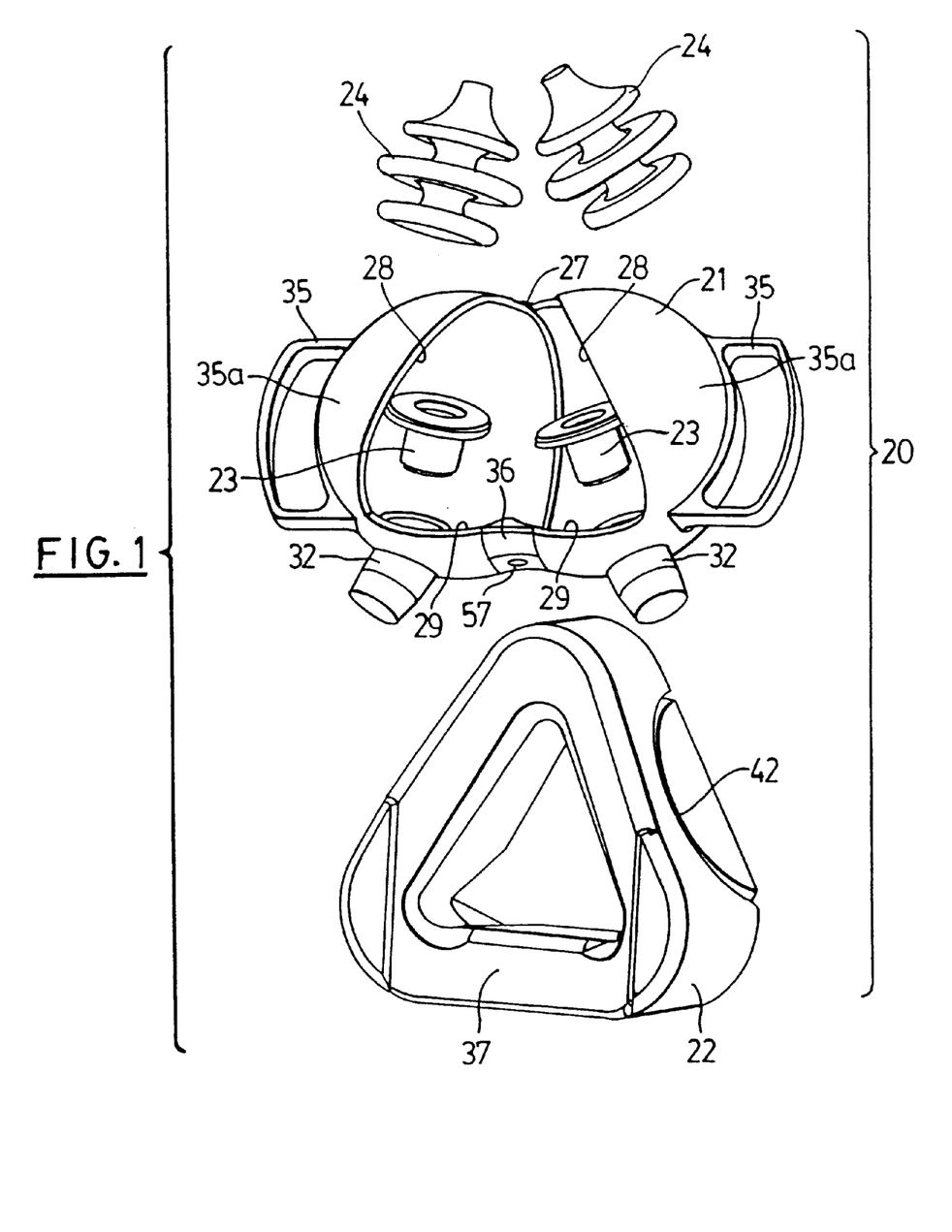
FIG. 1 shows an exploded view form the rear of a nasal mask in accordance with the invention.
Figure 6:
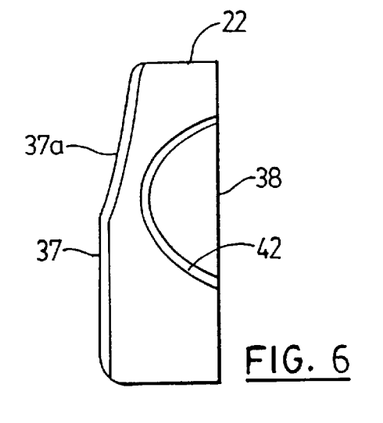
FIG. 6 is a side view of the interface portion of the mask.
Figure 7:
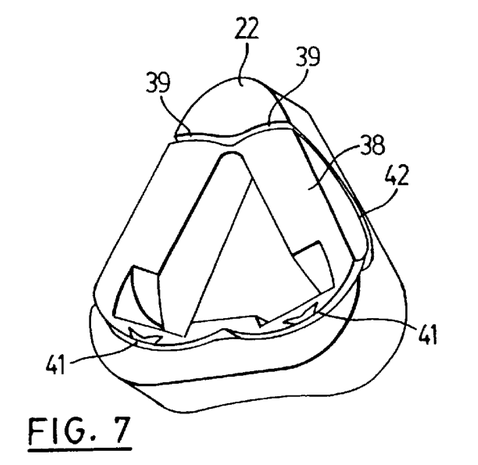
FIG. 7 is an isometric view from the front of the interface portion.

As best seen in FIGS. 1, 6 and 7, the interface 22 comprises a generally triangular endless member with rounded corners and generally planar rear and front sides 37 and 38 that, in use, engage with the patient's face and with the shell 21, respectively. As seen in FIG. 4, the rear side 37 of the interface member 22 may incline slightly forwardly upwardly at 37a, so that the member 22 tapers slightly in thickness upwardly and tends to conform to the patient's cheeks on each side of the nose.

Figure 2:
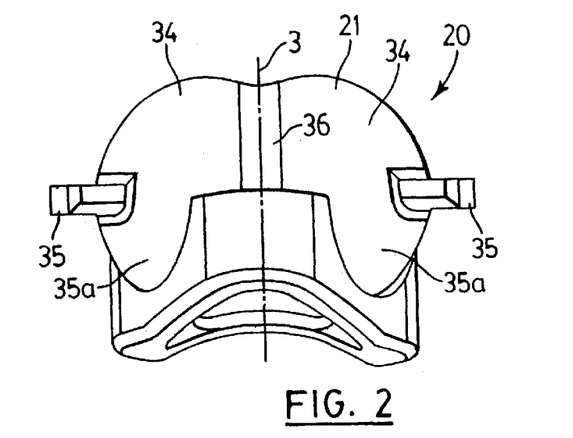
FIG. 2 is a top plan view of the mask of FIG. 1 in assembled condition.
Figure 3:
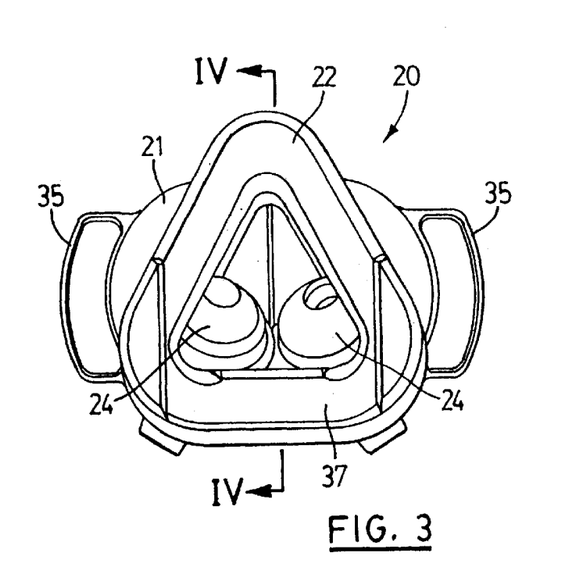
FIG. 3 is a view from the rear of the mask in the assembled condition.

The upper portion of the front side 38 of the interface member 22, as best seen in FIG. 7 is formed with a series of part circular grooves that receive the edges of the shell portion 21 when the interface is applied to the shell portion in the assembled condition as seen in FIGS. 2 to 4. As best seen in FIG. 7, these grooves are symmetrical about the median plane and comprise upper part circular grooves 39 that receive the bridge portion 36 and upper portions of the edges 28, and lower part circular grooves 41 that receive the lower edges 29 and lower portions of the side edges 28. Further, the sides of the interface portion 22 are formed with part circular grooves 42 that receive the intermediate portions of the side edges 28.

Figure 4A:
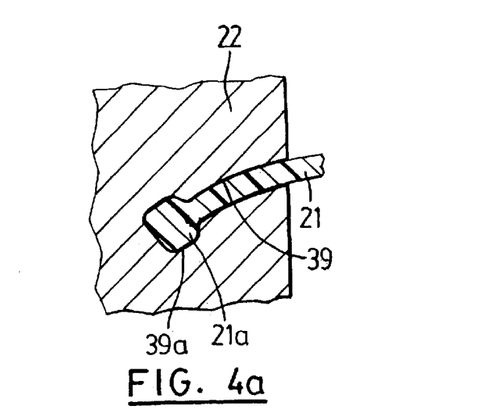
FIG. 4a is a partial cross-sectional view on an enlarged scale showing a modification of the structure of FIG. 4.
Figure 5:
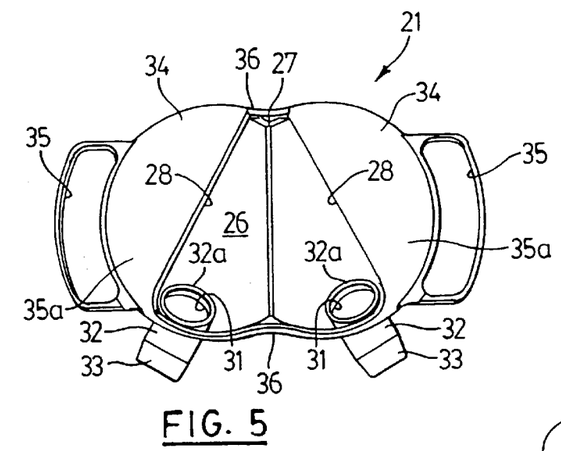
FIG. 5 is a view from the rear of the shell portion of the mask.

As best seen in FIG. 4, the grooves preferably penetrate a depth of at least about 25% of the thickness of the interface 22. Preferably, the grooves are slightly narrower than the thickness of the shell 21, so that there is a resilient reaction tending to cause the sides of the grooves to grip tightly on the edges of the shell 21. As shown in FIG. 4a, the edges of the shell 21 may be formed with a thickened bead 21a, and the bottom of each of the grooves such as groove 39 in the interface 22 may be formed with an enlarged recess 39a of somewhat smaller dimensions than the bead 21a, so that there is a resilient reaction tending to cause the material of the interface 22 to grip resiliently on the enlarged bead 21a, and improve the security of attachment of the interface 22 to the shell 21.

It will be noted that the interface member 22 is removably connected to the shell portion 21 so that it can be detached and a somewhat smaller or larger interface member substituted, in order to improve the fit of the interface member to the face of the patient.

Optionally, the mask may be used with nasal pillows 24 that are mounted on pillow engaging members 23. However, the use of such nasal pillows is not essential, and it is contemplated the mask may be used without such nasal pillows.

Figure 10:
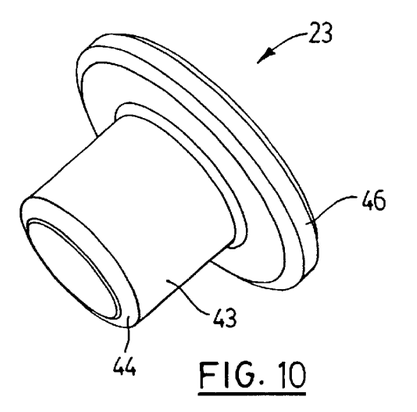
FIG. 10 is an isometric view from the rear and below of a disk member optionally forming part of the mask.
Figure 11:
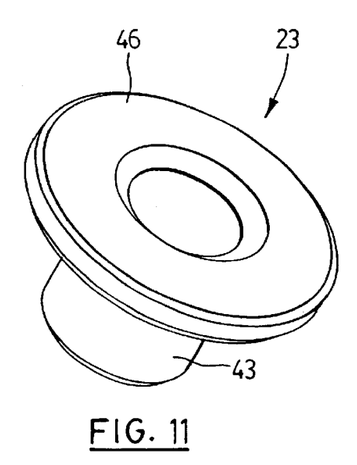
FIG. 11 shows an isometric view from above and from one side of the disk member.

As seen in FIGS. 10 and 11, the pillow engaging members 23, which may be molded of rigid plastics material, comprise hollow cylindrical stem portions 43 with tapering lower ends 44, and formed integrally with an enlarged disk element 46.

Figure 8:
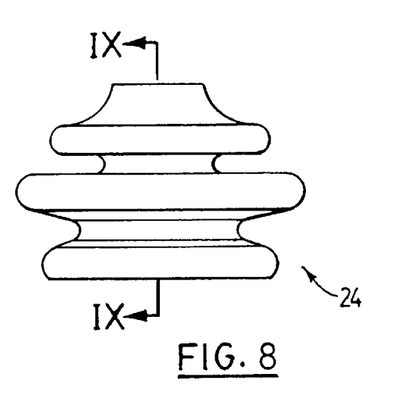
FIG. 8 is a side view of a nasal pillow optionally forming a portion of the mask.
Figure 9:
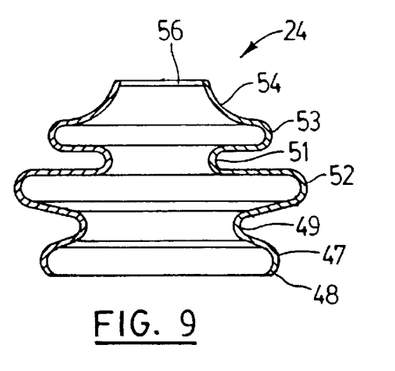
FIG. 9 is a cross-section along the line 9—9 in FIG. 8.

The nasal pillows 24, as best seen in FIGS. 8 and 9 are preferably formed of a highly resiliently deformable soft plastics material, for example soft silicone rubber composition.

The pillow is of a generally corrugated or accordion-pleated structure have a wide base portion 47 with re-entrant lower edges 48, relatively narrow intermediate portions 49 and 51, and relatively wide portions 52 and 53, the upper most of these terminating in an upwardly arcuately tapering tip 54 having a circular opening 56 at the upper edge.

In use, a disk element 46 of a member 23 is inserted within one of the wider portions 48, 52 or 53 of the nasal pillow 24 by stretching the material of the pillow 24, so that the disk element 46 snap-fits within one of the wider portion. The nasal pillows together with the members 23 are then inserted within the mask, and the stem portions 43 inserted within the inwardly extending cylindrical tubular portions 32a of the shell 21, as seen in FIGS. 3 and 4. The position of the pillows 24 within the mask may be adjusted to enable the tapering tip portions 54 of the pillows to engage snugly and in a leak free manner within the nostrils of a patient. This adjustment is effected by engaging the disk element 46 with a higher or with a lower one of the wider portions 47, 52 or 53.

Desirably, the shell 21 is provided with a small vent hole 57 in a lower portion of the bridge portion 36 of the shell, so that excessive pressure does not build up within the shell 21, for example when the mask 20 is applied and tightened to the user's face. If desired, this hole 57 may be plugged with a tight-fitting resilient e.g. rubber plug.

Figure 12:
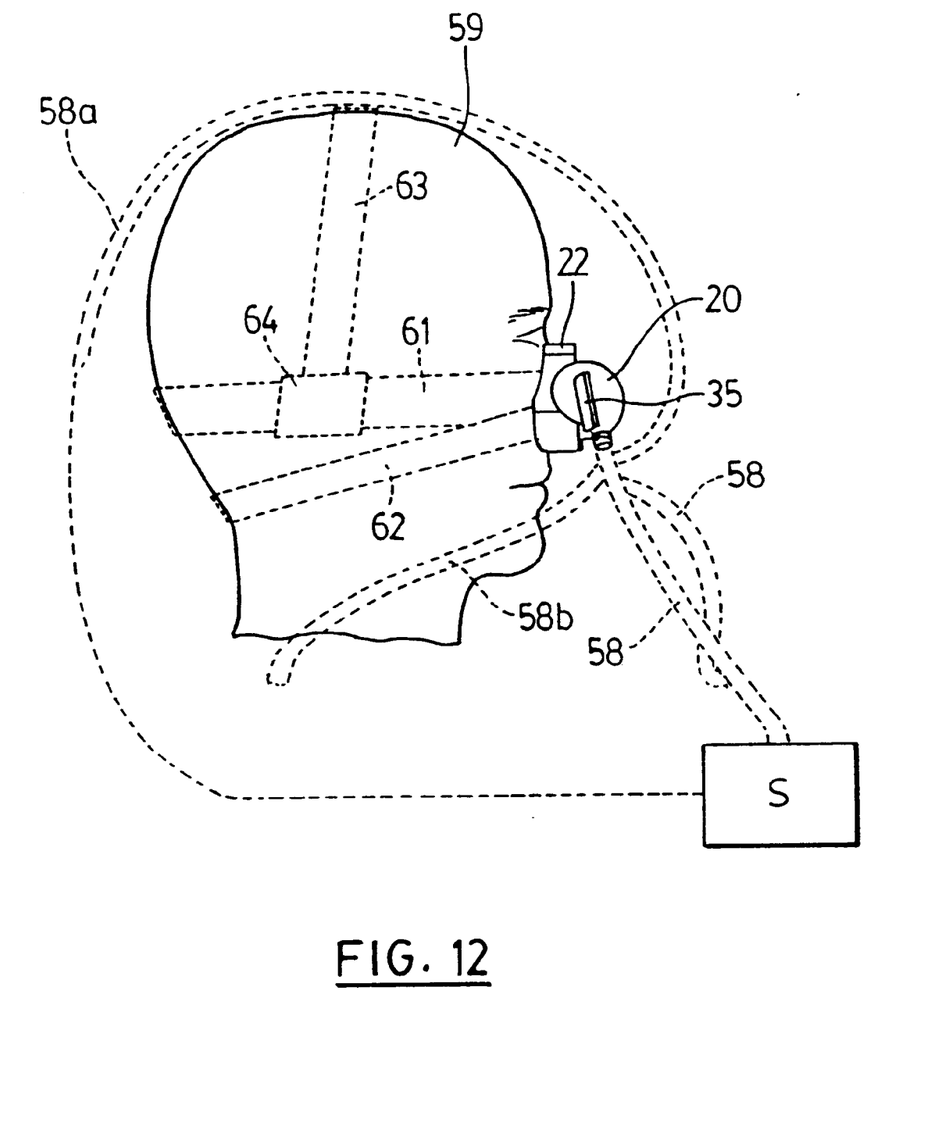
FIG. 12 shows somewhat schematically the mask worn by a patient.

In use, as seen in FIG. 12, a relatively small diameter gas or air supply hose 58 is push fitted over each outer cylindrical tubular portion 32, as shown in broken lines in FIG. 12, and is connected to a source S of air or other gas to be supplied to the patient. A strap or straps are attached through the strap lugs 35, and are passed around the head 59 to retain the mask 20 with the interface 22 pressed firmly and in a leak free fashion against the bridge of the nose, upper lip and cheeks on either side of the nose as seen in FIG. 12. Preferably, as seen in FIG. 12, the straps comprise a first strap 61 passing around the back of the patient's head 59, a second strap 62 passing around the head 59 at a region lower than strap, and a third strap 63 connected to intermediate portions 64 of strap 61 on each side of the patient's head 59 and passing over the top of the head 59. The straps 61 to 63 are usually resilient and may incorporate buckles or the like whereby the tension in each strap may be adjusted.

The relatively small diameter tube 58 exert only relatively small tensile forces in the direction away from the face of the patient and therefore only relatively small forces need-to be exerted by the straps 61 and 62 to retain the mask 20 and, as a result, excessive application of force to the user's face can be avoided. Pressure differentials over ambient existing in the inside of the shell 21 tend to bias the mask 20 toward the user's face as a result of the reaction of the pressure against the re-entrant portions 35a of the shell that extend rearwardly transversely inwardly between the lugs 35 and the edges 28 of the opening 26, so that excessive force exerted by the strap 59 can be avoided without risking leaks from the mask. The small diameter tubes may be easily oriented in any desired position relative to the mask 20. For example, they may be positioned downwardly below the mask as indicated for the tubes 58 in FIG. 12, they may be positioned centrally of the top of the user's head, as indicated by reference numeral 58a in FIG. 12, so that they are not obstructed if the user lies on one side, for example, when sleeping, or they may pass rearwardly on one side or on each side of the patient's head 59, as indicated by reference numeral 58b in FIG. 12, to a source placed behind the user.

When the nasal pillows 24 are employed, an especially leak free delivery of gas to the patient's airways can be provided, so that gas supplied at a selected pressure from the source S can be delivered to the patient without leaks and pressure loss occurring.

Figure 13:
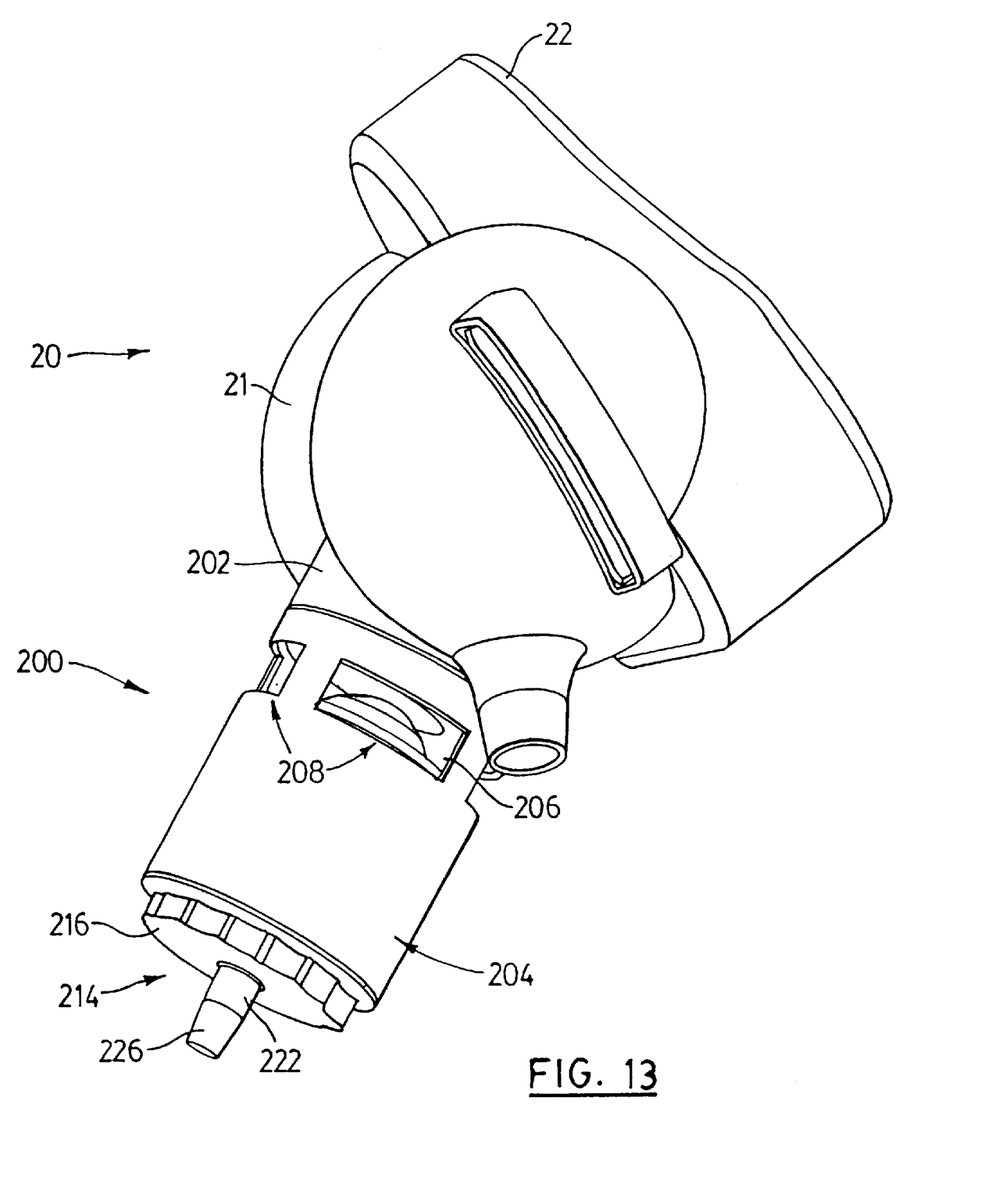
FIG. 13 shows a perspective view from the side of the combination of the mask and a balloon exhalation valve in accordance with the present invention.

Reference is now made to FIG. 13, which shows a mask 20 in combination with a balloon exhalation valve 200 in accordance with the present invention. The balloon exhalation valve 200 includes a casing 204, a balloon 206 and a source attachment 214. The source attachment 214 provides a mechanism for attaching a source of air or other gas and for securing the balloon 206 to the casing 204. The casing 204 is fitted upon an exhalation outlet 202.

Figure 15:
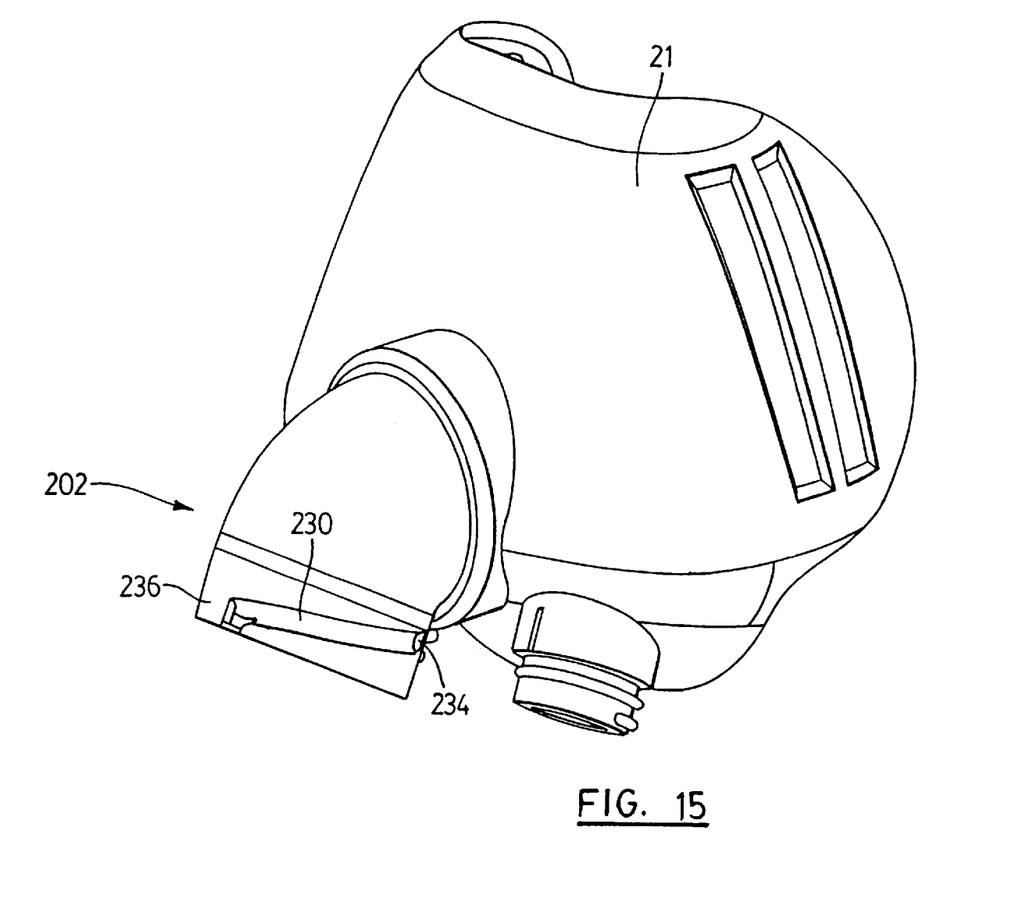
FIG. 15 shows an isometric view of the mask including an exhalation outlet.

Reference is now made to FIG. 15, which shows the shell 21 portion of the mask 20, including the exhalation outlet 202. In the preferred form, the exhalation outlet 202 is a tubular elbow formation extending substantially horizontally outwardly from an orifice in the front of the shell 21 and angling downwardly from its initially substantially horizontal position. The exhalation outlet 202 is preferably integrally formed with the shell 21 and defines a flow passage from its outermost end 236 through to the interior of the shell 21.

At least one groove 230 is formed in the outer surface of the exhalation outlet 202, beginning at the outermost end 236 of the exhalation outlet 202 and extending substantially circumferentially and somewhat longitudinally about the outer surface of the exhalation outlet 202. The groove 230 is provided with a locking recess 234 at its end furthest from the outermost end 236 of the exhalation outlet 202. A small ridge extending across the width of the groove 230 delineates the locking recess 234. The locking recess 234 comprises a short groove in the surface of the exhalation outlet 202 extending longitudinally towards the outermost end 236 of the exhalation outlet 202 and being in communication with the groove 230. The groove 230 is intended to cooperate with a cam (not shown) formed upon the inner surface of the casing 204 (FIG. 13). The casing 204 fits over the exhalation outlet 202 and the cam cooperates with the locking recess 234 and snaps over the ridge within the groove 230 to frictionally secure the casing 204 to the exhalation outlet 202.

Figure 14:
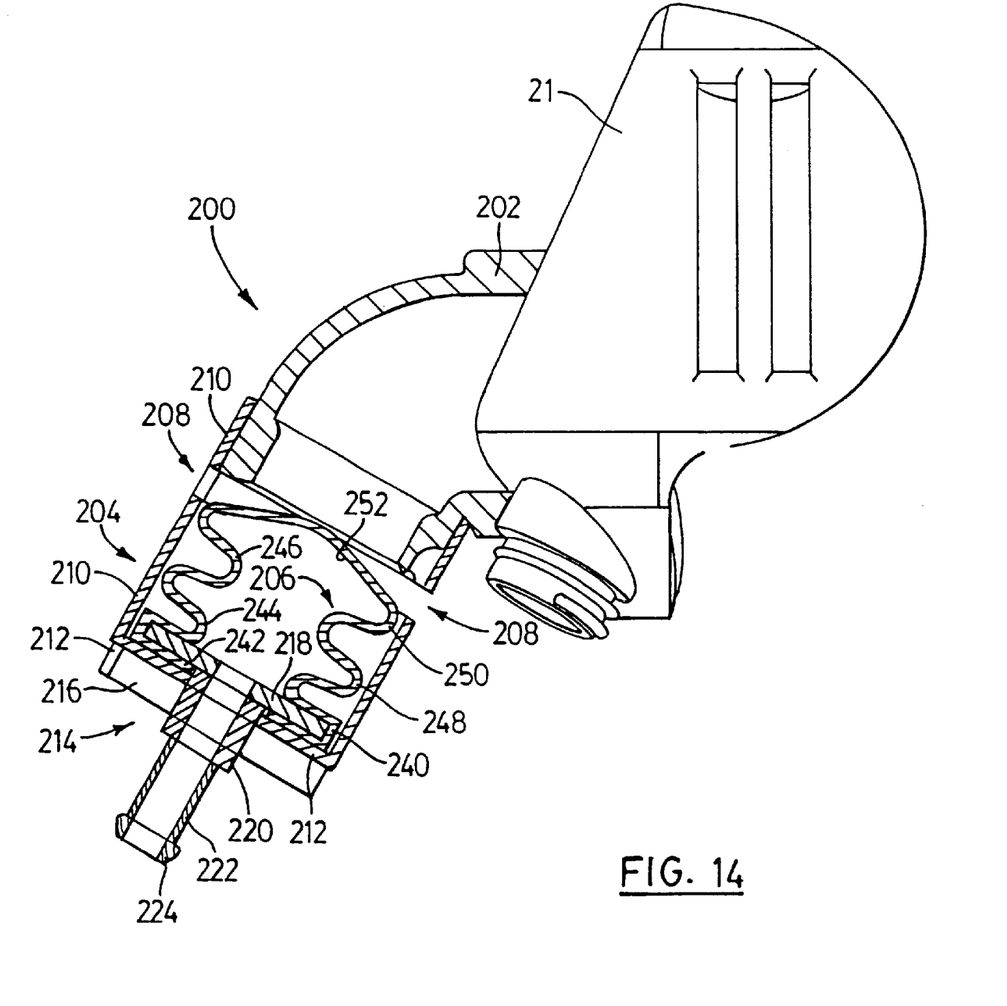
FIG. 14 shows a side view of the shell portion of the mask together with a partial cross-section of the balloon exhalation valve about a vertical center-line.

Referring now to FIG. 14, there is shown a cross-section of the exhalation outlet 202 and the balloon exhalation valve 200 along a vertical axial plane. The casing 204 comprises a tubular portion 210 that fits over the exhalation outlet 202 and a circular bottom face 212 having a circular passage therethrough centred about its axis. The tubular portion 210 has holes 208 defined therein and located proximate to that part of the tubular portion 210 which fits over the exhalation outlet 202, such that the holes 208 provide a flow passage from outside the casing 204 to the interior of the exhalation outlet 202. The casing 204 may, for example, be molded of a stiffly resilient plastics material.

The balloon 206 is contained within the casing 204 and is preferably formed of a highly resiliently deformable soft plastics material, for example soft silicone rubber composition. Similar to the pillows 24, the balloon 206 is of a generally corrugated or accordion-pleated structure having a wide base portion 240 with re-entrant lower edges 242, relatively narrow intermediate portions 244 and 246, and relatively wide portions 248 and 250, the uppermost of these terminating in a semi-spherical end 252.

The source attachment 214 comprises an inlet tube 222 upon the upper end of which is fixed a circular disk 218 with a central passage therethrough to communicate with the interior of the inlet tube 222. The inlet tube 222 further includes a threaded collar 220 proximate to the circular disk 218 and a ring 224 about the outer circumference of the lower end of the inlet tube 222.

A source hose for providing air or another gas to the balloon exhalation valve 200 is push fitted over the inlet tube 222. The ring 224 frictionally resists detachment of the source hose. The source attachment 214 also includes a nut 216 adapted to engage the threaded collar 220. Like the casing 204, the source attachment 214 may, for example, be molded of a stiffly resilient plastics material.

In another embodiment, the ring 224 is replaced by a tapered portion 226 (FIG. 13) to more easily accommodate push fitting an air supply hose upon the inlet tube 222.

As shown in FIG. 14, the wide base portion 240 of the balloon 206 is fitted over the circular disk 218, thereby securing the balloon 206 to the source attachment 214. The interior of the balloon 206 is in sealed communication with the flow passage through the source attachment 214. Accordingly, gas supplied to the source attachment 214 will inflate the balloon 206.

The balloon 206 and circular disk 218 are contained within the casing 204 and the inlet tube 222 and threaded collar 220 extend through the circular bottom face 212 of the casing 204. The nut 216 and threaded collar 220 cooperatively secure the source attachment 214 to the casing 204, thereby pinching the re-entrant lower edges 242 of the balloon 206 between the circular disk 218 and the circular bottom face 212 providing a sealed chamber within the balloon 206 and source attachment 214 to which gases are supplied.

In operation, the holes 208 in the casing 204 provide an exhalation flow path through the exhalation outlet 202 and the interior of the shell 21. When, during inhalation, the patient is supplied with air or other gases through the supply hose 58 and cylindrical tubular portions 32 (FIG. 12), the balloon 206 is inflated by a supply of gas through the source attachment 214. When inflated, the tip 252 and uppermost wide portions 250 of the balloon 206 expand upwards and radially within the casing 204, sealing the holes 208 and the outermost end 236 of the exhalation outlet 202, thereby preventing the escape of any gases from the interior of the mask 20.

To permit exhalation, the balloon 206 is deflated by the release of gas back through the source attachment 214, thereby re-opening the passageway from the interior of the mask 20 through the exhalation outlet 202 and out the holes 208 in the casing 204.

Accordingly, the balloon 206 is cyclically inflated and deflated to match the rhythm of inhalation and exhalation by the patient. Control over the inflation and deflation of the balloon 206 is exercised by a controller (not shown) at the source of the gas.

Advantageously, the mask 20 in combination with the balloon exhalation valve 200 alternately provides an obstruction free air passage for exhalation and a sealed interior for inhalation, thereby reducing leakage of air or other gas supplied to the patient and enabling easier breathing. The location of the balloon exhalation valve 200 in close proximity to the mask 20 and, therefore, the use's face reduces the dead space within which $CO_2$ can accumulate.

The present invention may be embodied in other specific forms without departing from the spirit or essential characteristics thereof. Certain adaptations and modifications of the invention will be obvious to those skilled in the art. Therefore, the above discussed embodiments are considered to be illustrative and not restrictive, the scope of the invention being indicated by the appended claims rather than the foregoing description, and all changes which come within the meaning and range of equivalency of the claims are therefore intended to be embraced therein.

I claim:

1. A nasal mask, said nasal mask comprising:
   a shell portion, said shell portion defining a hollow enclosure with a rearwardly facing opening defined by edge portions of the shell portion, and wherein the shell portion is at least generally symmetrical about a median plane, said shell portion having two gas inlet orifices disposed one on each side of the median plane, a front of said shell portion having an exhalation orifice approximately centered on the median place and, adjacent said exhalation orifice, an outwardly extending tubular elbow formation defining a flow passage through said exhalation orifice; and
   a balloon exhalation valve comprising a hollow tubular casing having a lower end face with a central passage therethrough, an inlet tube securely attached to said lower end face of said casing and passing through said central passage, and a balloon disposed within said casing, a mouth of said balloon being in sealed communication with said inlet tube, wherein an upper end of said casing is removably connected to said outwardly extending tubular elbow formation, and wherein said casing has an outlet orifice disposed proximate said outwardly extending tubular elbow formation, said outlet orifice defining a flow passage from said exhalation orifice through said casing, and wherein said balloon seals said outlet orifice when said balloon is inflated.

2. A nasal mask as defined in claim 1, wherein said balloon comprises a generally tubular corrugated balloon member having a rounded tip, a plurality of relatively narrow intermediate portions and a plurality of relatively wide intermediate portions.

3. A nasal mask as defined in claim 2, wherein said inlet tube further comprises a disk member disposed about an upper end of said inlet tube, whereby the balloon is secured to said disk member by engaging said disk member in a selected relatively wide intermediate portion of said balloon.

4. A nasal mask as defined in claim 3, wherein said inlet tube further comprises a threaded collar disposed about said inlet tube and a nut adapted to engage said threaded collar and secure said inlet tube to said casing, and wherein said balloon is pinched between said lower end face and said disk member.

5. A nasal mask as defined in claim 1, wherein an external surface of said outwardly extending tubular elbow formation has a channel formed therein, said channel beginning at an outer edge of said outwardly extending tubular elbow formation and extending substantially circumferentially and somewhat longitudinally in said external surface, and wherein an interior wall of said casing has formed thereon a cam, said cam adapted to cooperate with said channel to secure said casing to said outwardly extending tubular elbow formation.

6. The nasal mask as defined in claim 5, wherein said channel further includes a locking mechanism proximate to an end of said channel furthest from said outer edge of said outwardly extending tubular elbow formation, said locking mechanism adapted to cooperate with said cam to frictionally prevent removal of said casing from said outwardly extending tubular elbow formation.

7. The nasal mask as defined in claim 6, wherein said locking mechanism comprises a ridge disposed transversely within said channel.

8. A nasal mask for use by a patient, said nasal mask comprising:
   a shell, said shell defining a hollow enclosure with a rearwardly facing opening for engaging the patient's face, said shell having an exhalation orifice therethrough; and
   a balloon valve coupled to said shell, said balloon valve including a balloon having an inflated position and a deflated position for sealing and unsealing, respectively, said exhalation orifice, and wherein with said balloon in said deflated position said exhalation orifice provides a flow passage between the exterior of said nasal mask and the interior of said hollow enclosure.

9. The nasal mask claimed in claim 8, wherein said balloon valve includes a casing in sealed communication with said exhalation orifice, said casing containing said balloon and said casing having an outlet orifice proximate said exhalation orifice providing said flow passage to the exterior of said shell when said balloon is in said deflated position, and wherein in said inflated position said balloon obstructs said flow passage.

10. The nasal mask claimed in claim 9, wherein said balloon has a mouth and said casing includes an inlet tube in sealed communication with said mouth, said inlet tube being adapted to receive a supply of gas for inflating said balloon.

11. The nasal mask claimed in claim 9, wherein said shell includes an integrally formed outwardly extending tubular formation circumscribing said exhalation orifice for engaging said casing.

12. The nasal mask claimed in claim 8, wherein said balloon valve is in close proximity to said shell.

13. A nasal mask, said nasal mask comprising:
  a shell portion, said shell portion defining a hollow enclosure with a rearwardly facing opening defined by edge portions of the shell portion, and wherein the shell portion is at least generally symmetrical about a median plane, said shell portion having two gas inlet orifices disposed one on each side of the median plane, a front of said shell portion having an exhalation orifice approximately centered on the median place and, adjacent said exhalation orifice, an outwardly extending tubular elbow formation defining a flow passage through said exhalation orifice; and
  a balloon exhalation valve comprising a hollow casing having a lower end with a passage therethrough, an inlet tube securely attached to said lower end of said casing and passing through said passage, and a balloon disposed within said casing, a mouth of said balloon being in sealed communication with said inlet tube, wherein an upper end of said casing is removably connected to said outwardly extending tubular elbow formation, and wherein said casing has an outlet orifice disposed proximate said outwardly extending tubular formation, said outlet orifice defining a flow passage from said exhalation orifice through said casing, and wherein said balloon seals said outlet orifice when said balloon is inflated.

14. A nasal mask as defined in claim 13, wherein said balloon comprises a generally tubular corrugated balloon member having a rounded tip, a plurality of relatively narrow intermediate portions and a plurality of relatively wide intermediate portion.

15. A nasal mask as defined in claim 14, wherein said inlet tube further comprises a disk member disposed about an upper end of said inlet tube, whereby the balloon is secured to said disk member by engaging said disk member in a selected relatively wide intermediate portion of said balloon.

16. A nasal mask as defined in claim 15, wherein said inlet tube further comprises a threaded collar disposed about said inlet tube and a nut adapted to engage said threaded collar and secure said inlet tube to said casing, and wherein said balloon is pinched between said lower end and said disk member.

17. A nasal mask as defined in claim 13, wherein an external surface of said outwardly extending tubular formation has a channel formed therein, said channel beginning at an outer edge of said outwardly extending tubular formation and extending substantially circumferentially and somewhat longitudinally in said external surface, and wherein an interior wall of said casing has formed thereon a cam, said cam adapted to cooperate with said channel to secure said casing to said outwardly extending tubular formation.

18. The nasal mask as defined in claim 17, wherein said channel further includes a locking mechanism proximate to an end of said channel furthest from said outer edge of said outwardly extending tubular formation, said locking mechanism adapted to cooperate with said cam to frictionally prevent removal of said casing from said outwardly extending tubular formation.

19. The nasal mask as defined in claim 18, wherein said locking mechanism comprises a ridge disposed transversely within said channel.

* * * * *